United States Patent [19]

Yoon

[11] 4,302,187
[45] Nov. 24, 1981

[54] REMOVABLE ATTACHMENT FOR PARTIAL DENTURE

[76] Inventor: Han S. Yoon, 29-12, Kwan Hun Dong, Jong Ro Ku, Seoul, Rep. of Korea

[21] Appl. No.: 131,830

[22] Filed: Mar. 19, 1980

Related U.S. Application Data

[63] Continuation-in-part of Ser. No. 883,843, Mar. 6, 1978, abandoned.

[30] Foreign Application Priority Data

May 23, 1977 [KR] Rep. of Korea ................. 771212

[51] Int. Cl.³ .................................... A61C 13/22
[52] U.S. Cl. ................................ 433/172; 433/177
[58] Field of Search ............... 433/172, 177, 178, 182, 433/183, 191

[56] References Cited

U.S. PATENT DOCUMENTS

| | | | |
|---|---|---|---|
| 1,664,433 | 4/1928 | Seabrook | 433/182 |
| 1,825,593 | 9/1931 | Kempf | 433/208 |
| 1,976,085 | 10/1934 | Neurohr | 433/177 |
| 2,545,316 | 3/1951 | Stark et al. | 433/177 |
| 2,835,034 | 5/1958 | Plotnick | 433/178 |
| 3,427,718 | 2/1969 | Scott | 433/182 |
| 3,429,043 | 2/1969 | Andrews et al. | 433/183 |
| 3,672,057 | 6/1972 | Mays | 433/172 |
| 3,717,931 | 2/1973 | Konig | 433/177 |

FOREIGN PATENT DOCUMENTS

| | | | |
|---|---|---|---|
| 2427888 | 1/1975 | Fed. Rep. of Germany | 433/177 |
| 424085 | 5/1967 | France | 433/182 |

Primary Examiner—Gene Mancene
Assistant Examiner—John J. Wilson
Attorney, Agent, or Firm—Robert F. I. Conte

[57] ABSTRACT

The present invention provides a removable attachment for a partial denture with a sliding locking assembly. The locking assembly is provided with a relatively wide slot and narrower sliding slot or recess which has a major axis which is horizontal and at a right angle to the row of teeth, a locking member including a lock pin and a protruding member suitable for being retained in a recess of the denture and has a hole which may be engaged by the lock pin. The lock member is retained in position by a spring loaded pin and detent to receive the pin. The attachment may be easily operated by a fingertip without injury to the finger and no sudden separation of the partial denture is experienced. It may be used in cases where only the canine teeth of both sides exist as well as in cases where bilateral and/or unilateral teeth are missing. General dental instruments can be adapted for use with this attachment and no special instruments are necessary. The attachment can be fabricated from various standard dental materials and is reasonably economical.

10 Claims, 17 Drawing Figures (A)

(B)

(C)

(D)

(E)

(G)

(F)

REMOVABLE ATTACHMENT FOR PARTIAL DENTURE

CROSS REFERENCES TO RELATED APPLICATIONS

The present application is a continuation-in-part of U.S. application Ser. No. 883,843, filed on March 6, 1978, now abandoned, entitled a Removable Attachment for Partial Denture by Han Seok Yoon.

BACKGROUND OF THE INVENTION

A variety of removable attachments for partial dentures which are supported by adjacent teeth are known in the prior art. More specifically, the attachments commonly used by the dental profession are as follows:
1. The Chayes attachment developed in U.S.A.
2. The Ceka-anchor attachment developed in Belgium.
3. The Inoue attachment development in Japan.

These three attachments have common characteristics in their construction but also have common shortcomings.

They are inconvenient to remove at every mealtime and they are easily damaged due to the mechanical shock inflicted on the abutment teeth they are connected to. They can only be operated with special instruments. Finally, a sudden separation of a loosened partial denture can occur when even small amounts of wear or loosening of the attachment has occurred.

A more detailed explanation of the construction and operation of each of the attachments will illustrate the state of the prior art.

In the Chayes attachment a narrow and deep hole is disposed vertically in the upper side of a crown enclosing an abutment tooth. A protruder is provided at the corner of the partial denture and the protruder engages the vertical hole in the crown. Therefore, the Chayes partial denture is attached to the abutment teeth and prevents movement of the denture both lingually or bucally and left or right. This method of attachment however requires accurate partial denture size and is inconvenient since it is difficult to engage the protruder with a narrow hole each time it is to be attached. Furthermore, it requires the use of special instruments to operate and may only be fabricated from special high cost materials. As a result, both the cost of initial fitting and replacement is undesirably high.

The Ceka type attachment has a female unit joined to the abutment and a vertically oriented male member on the support of the mounted partial denture. It has a disadvantage in that everytime it is removed and reattached there is a great mechanical shock to the abutment tooth. Furthermore, the connector and protruder of this attachment can become worn due to abrasion and their ability to support the denture is thereby weakened. This type of attachment has another disadvantage in that it may not be used if the space available on the abutment tooth is less than 4 millimeters. Finally the cost of using the Ceka type attachment is high because it may only be used with expensive porcelain fused metal crowns.

In the Inoue type attachment a small protruder is mounted on the crown of an abutment tooth and a sleeve and lock pin are formed at the base portion of the partial denture. The lock pin is inserted in the protruder to fix the partial denture. In comparison with the other mentioned methods of attachment this method is comparatively safe but still has significant shortcomings. The sleeve and lock pin are difficult to operate by hand. Great damage can be done to the gingiva during attachment and it may only be used when a unilateral tooth is missing. Finally, this attachment is rather unsightly due to the external exposure of the lock pin.

It is therefore an object of the present invention to provide a removable attachment which does not require fabrication to narrow tolerances or from expensive materials and which may be economically replaced if refitting is necessary.

It is a further object of the present invention to provide an attachment for a partial denture which will not damage the abutting teeth or the gingiva.

Is is another object of the present invention to provide a removable attachment for a partial denture which may be used in a variety of applications including cases where the abutment teeth are few in number or somewhat damaged.

It is yet another object to the present invention to provide a removable attachment for a partial denture which may be installed without the need for specialized instruments, may be easily operated by the user, and is low in cost.

It is a further object of the present invention to provide a removable attachment for a partial denture having a support and a sliding lock member in the form of a tooth and where the sliding lock member has a locking pin which engages a hole in a protruder attached to an abutment tooth to secure the attachment and its denture.

It is an object of the present invention to provide an attachment for a partial denture where the motion of the locking member is limited by a limiting slot and a pin extending from the support member into the limiting slot.

It is a feature of the present invention to provide an attachment which may be used with two sets of artificial molars and being attached by lingual bar or a bar which can be disposed against one or more adjacent crowned natural teeth.

It is a further feature of the present invention to provide an attachment having a lock member which is retained in an opened or closed position by a lock pin resiliently mounted and which engages a detent.

SUMMARY OF THE INVENTION

The present invention relates to a removable attachment of a partial denture formed with a slidable lock assembly. This invention includes a relatively wide slot and a narrower slot or sliding recess formed so that in sectional view it is nearly horizontal and is at a right angle to the major axis of the teeth. A protruder projects from a crowned abutment tooth and a recess is formed in the corner of the support in order to receive the protruder. A pin mounted on the sliding lock member engages the hole in the protruder to secure the partial denture to the abutment tooth. The lock member is retained in a locked position by the use of a spring loaded pin and detent so that it will not move to an unlocked position while food is being chewed. The lock member is also provided with a slot and pin so that the locking member may move between a locked and unlocked position but will not be totally removed from the support.

The present invention may be used with a partial denture when only the canine teeth are present as well as when bilateral and/or unilateral teeth are missing. It may be easily dimensioned to accommodate dental features of various sizes and may be operated with dental instruments commonly in use.

It is secured by a mechanical connection; a pin and hole rather than being in direct contact with the abutment teeth and is fabricated from relatively low cost materials. Finally, it may be used where the dental space or clearance of the opposite tooth is less than 4 millimeters, a condition often encountered when teeth have been missing for a lengthly period of time.

The average patient can be provided with partial dentures which are superior in operation to those known in the prior art yet are lower in cost.

BRIEF DESCRIPTION OF THE DRAWINGS

FIG. 4 (b) is a perspective view showing the attachment with the locking member partially inserted;

FIG. 4 (c) is a perspective bottom view of the embodiment;

FIG. 4 (d) is a plan view of the attachment according to the invention;

FIG. 4 (e) is a sectional view taken along line A—A of FIG. 4d;

FIG. 4 (f) is a sectional view taken along line B—B of FIG. 4d;

FIG. 4 (g) is a sectional view along line C—C of FIG. 4d;

DETAILED DESCRIPTION OF THE INVENTION

Figure 1:
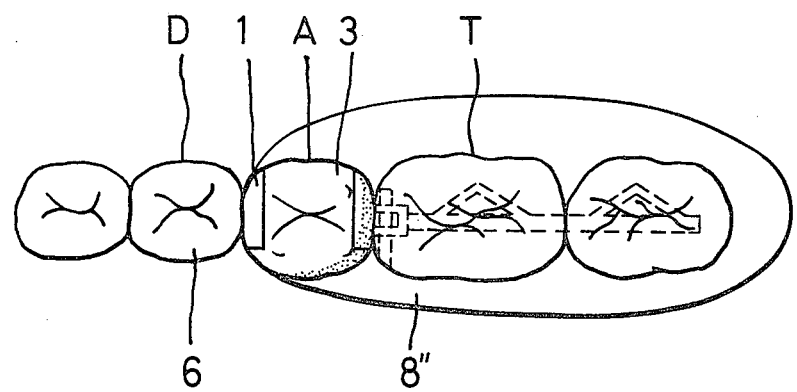
FIG. 1 is a plan view of an embodiment of the present invention.
Figure 2:
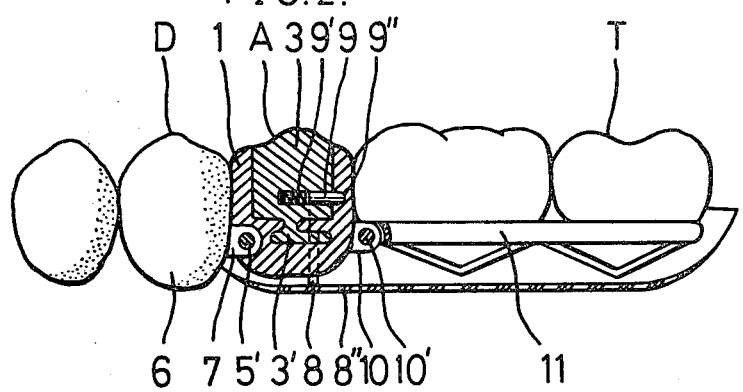
FIG. 2 is a sectional view of an embodiment of the present invention.
Figure 3:
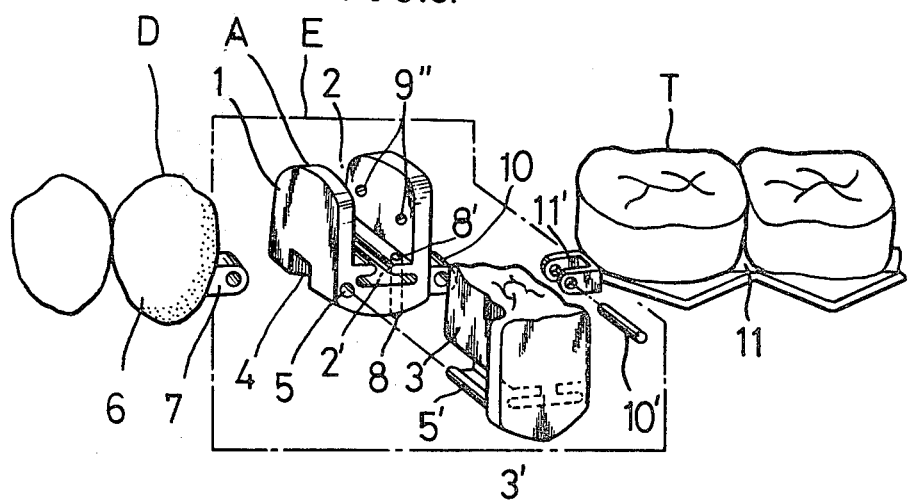
FIG. 3 is an exploded perspective view of an embodiment of the present invention.

Referring to FIGS. 1, 2, and 3 the structure of an attachment according to the present invention is shown. The support 1 of the attachment A is attached to the partial denture. It has relatively wide slot 2 and a narrower slot or slide recess 2' which has a cross-section form so that it is substantially horizontal and therefore at a right angle to the major axis of the teeth. As shown in detail in FIGS. 2 or 3 a lock member 3 has a surface in the form of a tooth and is provided with an extending or sliding member 3'. The member 3 rides in the recess 2 and the extending sliding member rides in recess 2' to prevent the lock member 3 from being displaced upwardly from the support 1. The lock member 3 may be moved lingually or bucally by simply pushing it with a fingertip. The support 1 includes a recess 4 and a pin hole 5 which receive the pin 5' mounted on the lock member. The abutment tooth D is provided with a crown 6 having a protruder 7 which also has a pin hole to receive the pin 5'. Therefore the connection of attachment A of the partial denture to the abutment tooth D can be accomplished by positioning the support so that the protruder on crown 6 of the abutment tooth D is inserted into the recess 4 of support 1. Then sliding lock member 3 is moved so that the lock pin 5' slides through the pin hole 5 and into the hole of the protruder 7.

Figure 4:
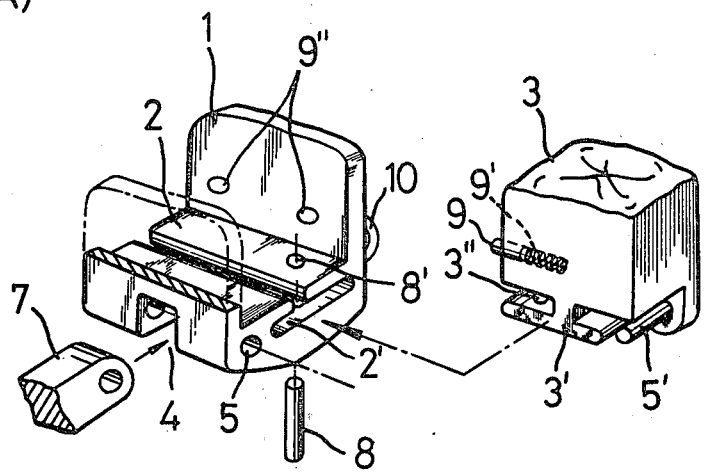
FIG. 4 (a) is an exploded perspective view of an embodiment of the present invention particularly showing a section of the attachment taken along line E of FIG. 3.
Figure 4:
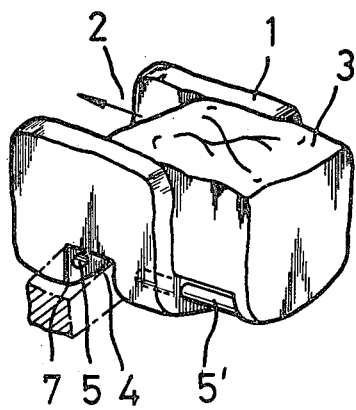
Figure 4:
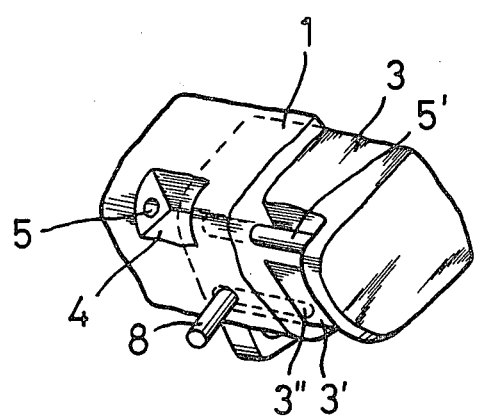
Figure 4:
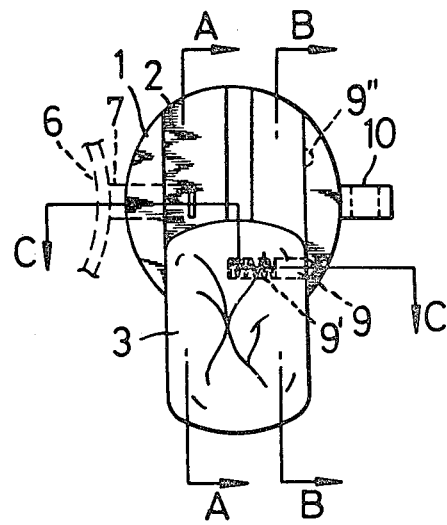
Figure 4:
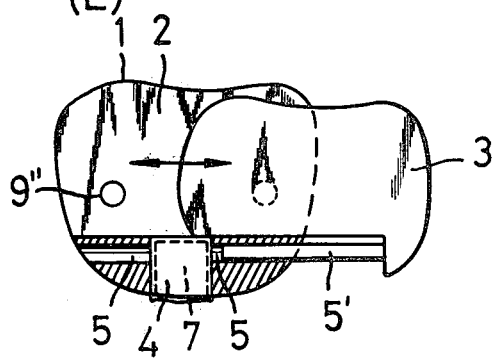
Figure 4:
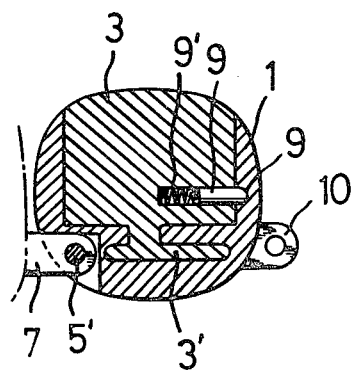
Figure 4:
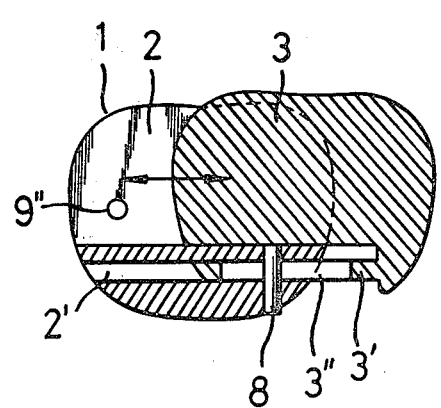

As can best be seen in FIG. 4c the extending slide member 3' has a guide slot 3" formed in one of its side portions. This slot 3" is provided to allow the lock member 3 to slide over a limited range within the support. During assembly the lock member 3 is inserted into the support and the pin 8 is inserted through the hole 8' and the slot 3" and permanently affixed there. Hence during normal operation the lock member may be slid back and forth between a locked and unlocked position but may not be totally disengaged from the support. Therefore the lock member cannot be accidentally dislodged or lost.

Figure 5:
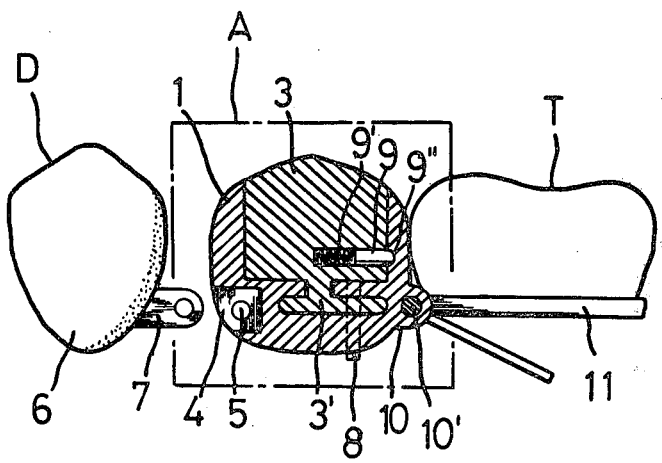
FIG. 5 is a sectional view showing the preferred embodiment of this invention.
Figure 6:
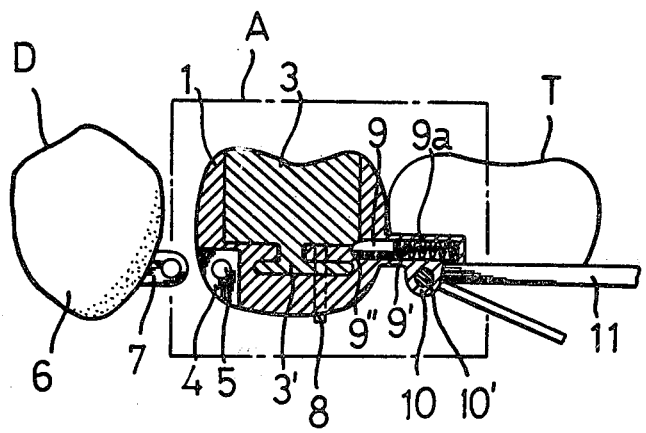
FIG. 6 is a sectional view illustrating an alternate embodiment of the present invention.

The lock member 3 is retained in its positions corresponding to a locked or unlocked condition by the use of a spring loaded lock pin and two detents. The placement of the pin and detent can best be seen in FIGS. 4a and FIG. 5 while an alternate construction is shown in FIG. 6. The first construction, as seen in FIGS. 4a and 5, uses a pin mounted in a hole in the lock member 3 and biased by spring 9'. The pin is urged against the wall of the support and will engage the detents 9". The placement of the detents correspond to the locked and unlocked positions of the pin 5'. When the lock member 3 is fully inserted into the support the pin 5' will engage the hole in the protruder 7 to secure the partial denture to the abutment tooth. The pin 9 will be retained in the left most detent indicated as 9" of FIG. 4a. When the lock member 3 is slid to its unlocked position and pin 5' disengages the protruder the pin 9 will engage the right most detent indicated as 9" in FIG. 4a. Thus the lock member is retained in either the locked or unlocked position but may be slid by finger pressure.

FIG. 6 shows an alternate arrangement of the locking pin and detents which is to be used when the lock member 3 is too small to acommodate the spring 9' and pin 9. In this case a hole is formed in the tooth of the partial denture T and may be provided with a sleeve 9a. The spring 9' urges the pin 9 against the lock member 3 and hence engages the detents 9" in the lock member 3. The result is the same as that obtained in the construction first presented i.e. the lock member is retained in either a locked or unlocked position unless finger pressure is applied to it.

This feature is important since it retains the lock member in a locked position when the denture is fixed in the mouth. Speech or the mastication of food will not accidentally misplace the lock member. Likewise when the denture is being inserted into the mouth the lock member must be in an unlocked position to allow the proper placement of the protruder within the recess 4. This feature prevents the lock member from accidentally moving to a locked position before it is properly placed.

The connector 10 protrudes from the side of the attachment opposite the recess 4 and is attached to the frame 11 by means of a connector 10'. A variety of different types of partial dentures can be mounted on the frame in accordance to the condition of the patient.

FIG. 5 shows a first embodiment of the standard type of attachment according to the present invention. This attachment is used in cases where the first premolar or second premolar or the like are defective but where there is a molar behind them. It can also be adapted in cases where all the teeth from the first premolar or second premolar to the molar are defective. The teeth are relatively wide and high and this attachment can be used in many cases where the upper and lower teeth are defective.

Referring to FIG. 5 this embodiment will be described in greater detail. The side portion of support 1 of the attachment A is provided with the recess 4 dimensioned to receive the protruder 7 which projects from the crown 6 of the abutting tooth D it is also formed with a relatively wide slot 2 and a sliding recess 2'. These are dimensioned to receive the lock member 3 which is in the form of a false tooth and has a sliding member 3' integrally formed with it and which is received by the lower and narrower section of the slot. Pin 9 and spring 9' are fitted by a hole in the lock member 3. The end of the pin is received by a detent 9" in the wall of the support. Once the lock member and support have been assembled pin 8 is inserted through a hole in the bottom of the support 1 and passes through a slot in the sliding member 3' so that the lock member cannot be displaced from the support. The frame 11 of the denture T is connected to the protruder 10 at the lower side portion of the support 1. When the partial denture is to be secured within the mouth this assembly is fitted over the protruder 7 and the locking member is operated to move the lock pin 5' through the opening in the protruder to thereby secure the partial denture in place.

FIG. 6 shows an alternate embodiment of the present invention where the tooth formed is not quite as tall as the one illustrated in FIG. 5. There is not enough room to mount the pin 9 and spring 9' within the lock member 3. Here the pin 9 and spring 9' is mounted within a sleeve 9a mounted on the frame 11 of the partial denture. The lock member 3 is provided with detents 9 to retain the lock member 3 in either its locked or unlocked position.

Figure 7:
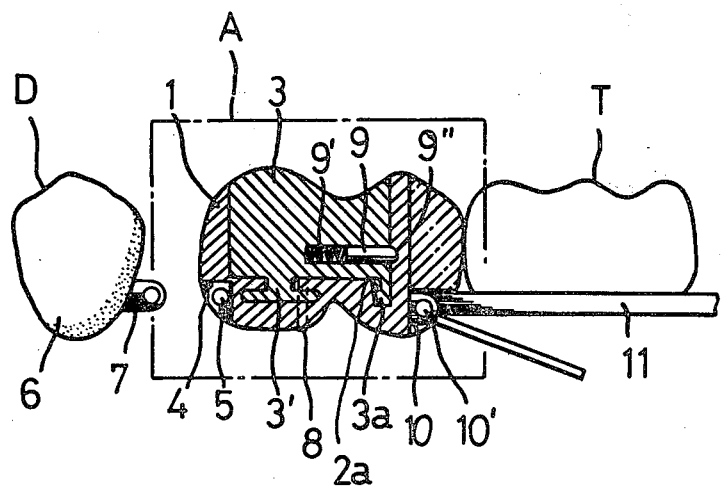
FIG. 7 is a sectional view showing another embodiment of the present invention.

FIG. 7 shows a third embodiment of the invention. Here the attachment takes the form of two teeth and thus is much wider than the other embodiments. The slot in the support is provided with a second slot 2a in its lower portion which is dimensioned to receive a second sliding protruder 3a which is formed as a integral member of lock member 3. Since the lock member is relatively large the pin 9 and spring 9' are mounted therein. Here again the frame 11 of the partial denture T is secured to the attachment by means of connector 10 and connecting pin 10'. It must be appreciated that the support and lock member may be fabricated to take the form of any number of teeth. Also the lock member and support may be provided with many different configurations of slots and protruding members to allow the lock member to slide relative to the support.

Figure 8:
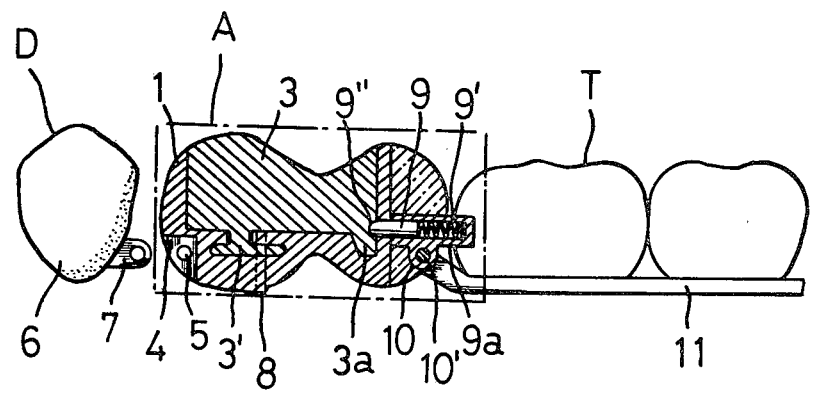
FIG. 8 is a sectional view illustrating yet another embodiment of the present invention.

FIG. 8 shows an embodiment of the invention which is similar to the multi-toothed arrangement of the embodiment shown in FIG. 7. However here the height of the lock member 3 is reduced and therefore the pin 9 and spring 9' cannot fit in the lock member 3. Here they are fitted into sleeve 9a which is mounted partially within the attachment itself and partially within the denture T. The detents 9" are formed within the lock member 3 at a position close to the secondary slot.

Figure 9:
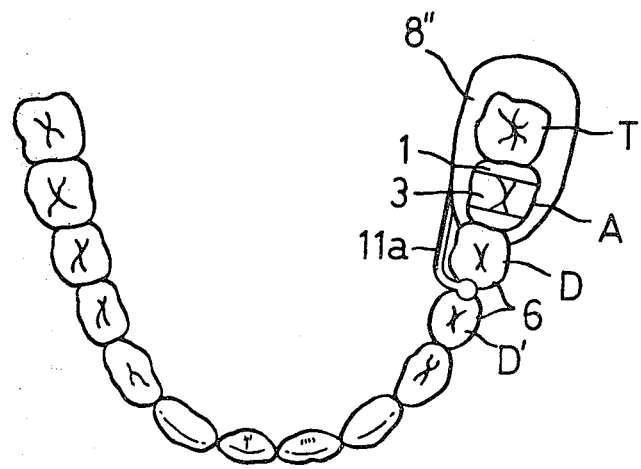
FIG. 9 is a plan view showing the present invention adapted for use with a unilateral tooth defect.

FIG. 9 shows a fifth embodiment of the invention, unilateral distal extension partial denture, which is useful when unilateral teeth are missing, e.g., when the first molar and second molars are defective. In this application the attachment A is constructed similar to the previous examples and is connected to the partial denture T which has a prosthetic gingiva 8". The lingual bar 11a is formed as an extension of the frame 11. The abutment tooth D and the next tooth D' are crowned to receive the end of the lingual bar 11a. When in place this attachment A is secured by means of the removable attachment. The prosthetic gingiva 8" is disposed against the toothless gum and the end of the lingual bar 11a is disposed against the crowns 6 of the abutment teeth D and D'. This is a significant improvement over the dentures known in the prior art which uses two bars which encircle the tooth on both the left and right sides. Hence this improved denture may be provided at a lower cost but is more comfortable than previous ones.

Another factor which reduces the cost of this denture is the fact that the abutment teeth may be crowned using any one of the special metals normally used, for example, gold alloy, regular alloy, or special alloy, etc., Costly procelain capping is not necessary.

Figure 10:
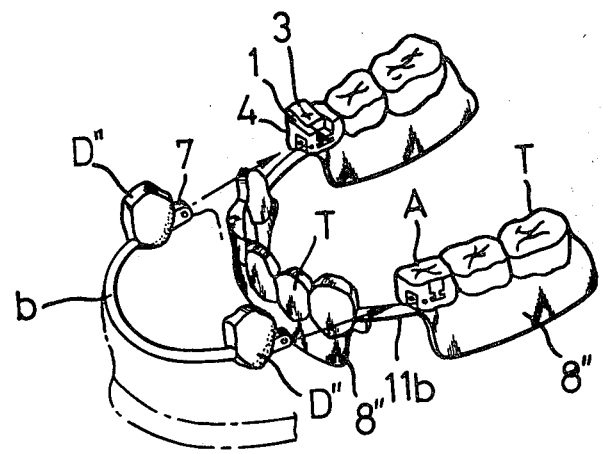
FIG. 10 is an exploded perspective view showing an embodiment this invention adapted for use with bilateral teeth defects.
Figure 11:
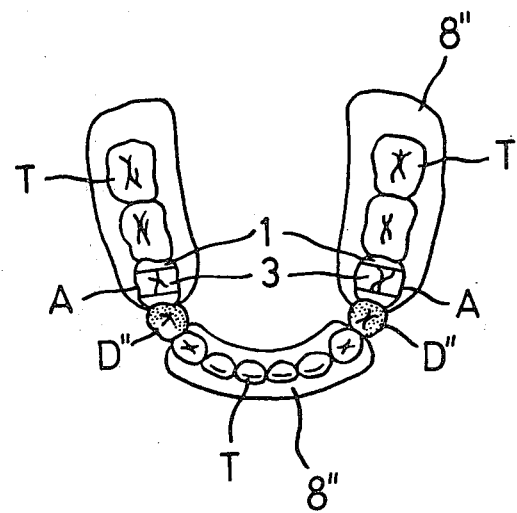
FIG. 11 is a plan view of the embodiment shown in FIG. 10.

FIGS. 10 and 11 show a denture which may be used where there are extensive bilateral tooth defects and only the canine teeth remain. Reinforcement bar B is connected to crowns mounted on the canine teeth D" which are each provided with protruders 7. Thereafter the denture is formed having the attachments A, teeth T and artificial gingiva 8". The lingual bar 11b connects the molar and incisor carrying portions of the frame. The denture is attached on either side by means of the attachment A engaging the protrusion 7 of the canine teeth. Here the abutment teeth are utilized without the need for cutting as would be the case if a Ceka-anchor arrangement was to be used.

An alternative to the form of the embodiment shown in FIGS. 10 and 11 is a bilateral distal extension partial denture used when molars and premolars are missing on both sides but the canines and incisors are healthy. In such a case a partial denture similar to the one shown in FIGS. 10 and 11 is used but the prosthetic incisors and associated prosthetic gingiva are omitted. They are replaced by a lingual bar which is dimensioned so that it will be positioned behind the natural incisors when the denture is in place. This lingual bar is joined to the molar carrying frame or to the attachment.

Al alternative to the use of a lingual bar in cases of unilateral defects is to support the partial denture by a telescopic crown. This is particularly useful when teeth between the canine and rearmost molar are missing. The telescopic crown is dimensioned to be received by the rearmost molar and the canine is provided with a crown having a protruder. The partial denture is constructed with the telescopic crown at one end and a connector, according to the present invention, at the other end. Thus when the partial denture is inserted one end is connected to the crowned canine by means of the connector and the other end is connected to the rear molar by means of the telescopic crown.

Thus it is apparent that the attachment described has several outstanding features. The sliding lock member and support with their associated pins and springs may be mass produced however they are easily adaptable for use with dentures custom fitted to each individual patient. The protruder can be attached to any tooth or tooth fragment which will retain a crown. No work on the abutment tooth is necessary except for the attachment of the crown. The attachment by means of the hole in the protruder and the locking pin on the attachment is elegantly simple yet secure. Since the attachment is fabricated in the shape of a tooth its use is far more cosmetically acceptable than devices known in the prior art.

While I have described my invention to some detail and in several embodiments, it will be apparent to those skilled in the art that various changes and modifications can be made without departing from the spirit of the invention. Therefore the invention should not be limited by the description above but only by the claims which follow.

That which I claim is:

1. A removable attachment for a partial denture comprising;
   (a) a support extending approximately the length of at least one tooth;
   (b) a lock member adapted to have its outer surface function as the artificial tooth;
   (c) one of the support or the lock member defining a receiving slot extending substantially the width thereof and having both wide and narrow slot sections and which is horizontal and at a right angle to the major axis of the denture;
   (d) an extending surface formed to slidably engage the receiving slot in a relatively tight fit and extending from the other of the support or lock member;
   (e) a protruding member which is adapted to be connected to and extend from an adjacent tooth;
   (f) a recess defined by the support member and dimensioned to receive the protruding member when the support member is positioned adjacent to the tooth from which the protruding member extends;
   (f) a lock pin formed on the lock member and extending therefrom and which engages the protruding member when the lock member is slid along the slot to thereby secure the support to the adjacent tooth; and
   (h) a means to attach the support to the partial denture.

2. The attachment according to claim 1 wherein the lock member defines a limiting slot and a pin extending from the support member and into the limiting slot to limit the sliding motion of the lock member within certain bounds.

3. The attachment according to claim 1 which further comprises a partial denture provided with two sets of artificial molars or pre-molars each having a removable attachment and being joined by a lingual bar.

4. The attachment according to claim 1 which further comprises a partial denture provided with a support bar, one end of which is attached to the partial denture and the other end of which can be disposed against one or more adjacent, crowned, natural teeth.

5. The attachment according to claim 1 in which said support extends the length of two or more teeth.

6. The attachment according to claim 1 wherein one of the lock member or support is further provided with an additional secondary extending surface and the other is additionally provided with a secondary receiving slot to receive the secondary extending surface.

7. The attachment according to claim 1 wherein the partial denture is further comprised of a lock means having a lock pin resiliently mounted in the lock member and a corresponding recess in the support member to receive the lock pin.

8. The attachment of claim 7 wherein the lock member defines the receiving slot.

9. The attachment of claim 8 wherein the lock member has a limiting slot formed in the base thereof and the support member has a hole which will axially align with the limiting slot, and a limiting pin inserted in the hole and passing through the limiting slot to permit limited sliding motion of the lock member relative to the support member.

10. The attachment according to claim 1 wherein the partial denture is further comprised of a locking means having a locked pin resiliently mounted in the support member and a corresponding recess in the lock member.

* * * * *